(12) United States Patent
Nilsson

(10) Patent No.: US 6,653,109 B1
(45) Date of Patent: Nov. 25, 2003

(54) METHOD OF PRODUCING DERIVATIVES OF LACTOSAMINE

(75) Inventor: Kurt Nilsson, Lund (SE)

(73) Assignee: Procur AB, Lund (SE)

( * ) Notice: Subject to any disclaimer, the term of this patent is extended or adjusted under 35 U.S.C. 154(b) by 0 days.

(21) Appl. No.: 08/666,542

(22) PCT Filed: Jan. 9, 1995

(86) PCT No.: PCT/SE95/00010

§ 371 (c)(1),
(2), (4) Date: Jun. 28, 1996

(87) PCT Pub. No.: WO95/18864

PCT Pub. Date: Jul. 13, 1995

(30) Foreign Application Priority Data

Jan. 6, 1994 (SE) .................................................. 9400034

(51) Int. Cl.[7] ........................... C12P 19/12; C12N 9/34; C12N 9/36

(52) U.S. Cl. .................. 435/100; 435/205; 435/206; 435/207; 435/209; 435/224

(58) Field of Search ................ 435/100, 205, 435/206, 207, 209, 224

(56) References Cited

U.S. PATENT DOCUMENTS

| | | | |
|---|---|---|---|
| 4,415,665 A | 11/1983 | Mosbach | 435/179 |
| 4,918,009 A | 4/1990 | Nilsson | 435/73 |
| 5,246,840 A | 9/1993 | Nilsson | 435/101 |
| 5,372,937 A | 12/1994 | Nilsson | 435/74 |
| 5,405,752 A | 4/1995 | Nilsson | 435/7.94 |

FOREIGN PATENT DOCUMENTS

| | | |
|---|---|---|
| WO | 9303168 | 2/1993 |
| WO | 9429477 | 12/1994 |

OTHER PUBLICATIONS

J. Carbohydrate Chemistry (1992), vol. 11, pp. 553–565.
Carbohydrate Research (1994), vol. 259, pp. 103–115.

*Primary Examiner*—Mary K. Zeman
(74) *Attorney, Agent, or Firm*—Smith, Gambrell & Russell, LLP

(57) ABSTRACT

Disclosed is a method of producing a compound with β1-4 linkage which contains the lactosamine structure involving reacting at least one donor substance GalβOR where R is an organic group, and at least one acceptor substance which is a glucopyranosamino derivative having the formula GlcNR"—R'", wherein NR" is an azido, 2-N-acetyl-, 2-N-phtalimido, or an organic group bound to the 2-N-group of glucosamine, wherein R'" is a glycosidically bound fluoro or is an O-, C-, N- or S-glycosidically bound aliphatic or aromatic compound, with the proviso that if NR" is NHAc then R'" is not OH and if NR" is not NHAc then R'" may be OH, in the presence of *Bullera singularis* or an E.C. group 3.2 glycosidase of essentially the same structure as an E.C. Group 3.2 glycosidase obtained from *Bullera singularis* to form the lactosamine derivative; and optionally isolating the compound with β1-4 linkage which contains the lactosamine structure.

16 Claims, No Drawings

METHOD OF PRODUCING DERIVATIVES OF LACTOSAMINE

INTRODUCTION AND BACKGROUND

The present invention describes a new method for the production of certain carbohydrate containing compounds related to glycoconjugates; namely, lactosamine derivatives and substances derived therefrom. In a further aspect the present invention relates to products produced by the above method as well as uses of the resulting products.

Glycoconjugates contain saccharide chains with from one up to twenty monosaccharide units and in which certain sequences have been shown to have biological activity, for example in the binding of different cells, pathogens, toxins, as well as antibodies or other proteins to cell surfaces, in cancer metastasis, in inflammatory processes, for instance selectin-carbohydrate interactions in the binding of white blood cells to the blood vessel wall, as a modifier of the biological activity and stability of glycoproteins, as immunogenic substances, which have potential in the vaccination against different diseases (See for instance Annual Review of Biochemistry, vol. 58 (1989), pages 309–350, and Current Opinion in Structural Biology, for example review articles in vol. 3 (1993) and references therein).

Structures containing the sequence Galβ1-4GlcNAc, called N-acetyl-lactosamine below, are especially of importance and are found for instance in glycoconjugate oligosaccharides of the lactosamine type. The structure is found in blood group structures, for instance Lewis-x (e.g. Galβ1-4 (Fucα1-3)GlcNAc), sialylated Lewis-x and 3'-sulfated Lewis-x, and is of importance in e.g. selectin-carbohydrate interactions (as reviewed by J. B. Lowe, in Molecular Glycobiology, pages 163–205, Fukuda and Hindsgaul, Eds., IRL Press at Oxford University Press, Oxford, 1994; see also Curr. Opin. Struct. Biol. vol. 3 (1993)).

It is of interest to be able to produce derivatives of lactosamine in large quantities for biological/clinical studies/tests, for example for inhibition of the selectin-carbohydrate interaction in vivo to inhibit/modify cell-mediated inflammatory processes (for instance in acute septic shock, ARDS, reperfusion injuries, rheumatoid arthritis, virus-induced pneumonia, psoriasis and the like).

Chemical methods known heretofore to produce N-acetyl-lactosamine and derivatives thereof have demanded multi-step synthesis and are often expensive and labor intensive. Enzymatic methods used before the present method were mainly based on the use of galactosyltransferase (EC 2.4), a cofactor dependent enzyme which requires UDP-galactose as a glycosyl donor (e.g. Wong et al., J. Org. Chem. (1982), pages 5416–5418). This type of enzyme also has disadvantages as high acceptor selectivity and exhibits low efficiency with unnatural acceptors, for instance derivatives of glucosamine (e.g. as reviewed by Khan and Hindsgaul in Molecular Glycobiology, pages 206–229, Fukuda and Hindsgaul, Eds., IRL Press at Oxford University Press, Oxford, 1994). For a general review of enzymatic methods, see K. G. I. Nilsson, Trends in Biotechnology, 1988, p. 256–264 (the nomenclature used in that review article and in this application follow the same IUPAC-rules). Glycosidases have been used to produce N-acetyl-lactosamine and N-acetyl-allolactosamine from galactosides and N-acetyl-glucosamine (Sakai et al., J. Carbohyd. Chem, 11: 553–565, 1992).

Earlier methods with glycosidases (EC 3.2) for production of derivatives of N-acetyl-lactosamine gave generally low yields because of low or wrong regioselectivity. Thus, for example, α-galactosidase from *E. coli* or from ox-testes give solely Galβ1-6GlcNPht, (K. G. I. Nilsson, unpublished result; Pht symbolizes a phthalimido group which generally is used as a temporary protection group on the amino group of glucosamine) when lactose is used as the glycosyl donor and GlcNPht is used as the acceptor.

SUMMARY OF THE INVENTION

The present invention describes a method which with unexpectedly high specificity gives the β1-4 linkage in the synthesis of different lactosamine derivatives, using abundant donor substances such as lactose and other low cost galactosyl donor substances. In one embodiment of the invention, the method is carried out by using the yeast *Bullera singularis* as a catalyst (classified as *Bullera singularis* according to Yeasts, second edition by Barnett et al., Cambridge University Press, 1990).

In a second embodiment, the process of the invention is carried out by using enzymes (which belongs to the group of glycosidases, EC Group 3.2), preferably in a crude, partially isolated or isolated form, especially β-galactosidase from *Bullera singularis* but also other β-galactosidase e.g. recombinant, of the same structure or of a similar structure (e.g., containing similar active site structure) as the one from *Bullera singularis*.

DETAILED DESCRIPTION OF THE INVENTION

According to the more detailed aspects of the present invention, the process for producing lactosamine derivatives can be carried out as an equilibrium (reversed hydrolysis) reaction or preferably as a kinetic (transglycosylation) reaction. As is known in the art, the principles of an equilibrium reaction and a kinetic reaction are well understood (e.g. see K. G. I. Nilsson, Trends in Biotechnol. (1988), pages 256–264).

In the case where the reaction is carried out as a transglycosylation reaction, the glycosyl donor is a glycoside, e.g. of D-galactose (Gal) modified in the C-1 position (anomeric position) but it can also be an oligosaccharide, such as lactose (Galβ1-4Glc or aglycoside thereof, e.g.:

GalβOR+GlcNR"—R'"→Galβ1-4GlcNR"—R'"+ROH

R can be a glycosidically linked organic group, for example sugar (e.g. $C_nH_{2n}O_n$ or $C_nH_{2n-2}O_{n-1}$ such as glucose), lower alkyl group (e.g. -Me, -Et) or an aromatic group (e.g. phenyl (-Ph), umberriferyl or m-, o-, or p-nitrophenyl group), preferably R is Glc (glucose) or nitrophenyl. Other glycosides (e.g. F-, N- or S-glycosides) may be selected.

It is known in the art that glycosidases allow some modification of the glycon part (i.e., the galactosyl part in the present invention) of the glycosyl donor. Therefore, in addition to GalβOR, donors where the galactosyl part have been partially modified in a way still allowing the transglycosylation reaction to occur, resulting in the β1-4 linkage between the glycon part of the glycosyl donor and the glucosamine derivative, can be selected by the person skilled in the art for use with the method according to the present invention. Examples of such modifications of the glycon are modifications where at least one of the hydroxyl groups have inverted configuration (e.g. inversion in position 4 means that Gal is substituted for by Glc, that is GlcβOR, i.e. a β-glucoside, is used as donor), or where one of the hydroxyl groups of Gal has been modified or substituted for by an inorganic (e.g. -F, -H) or an organic group, e.g. a lower alkyl (e.g. methyl), allyl or an acetyl group. The selection of such a donor in the method according to the invention thus gives a β1-4 linked product in which the galactosyl part is correspondingly modified. Products of the type R'-Galβ1-4GlcNR"—R'" may thus be prepared where R'-Gal relates to a modified glycon of the glycosyl donor. In the case of a transglycosylation reaction, the glycosyl donor in the scheme shown below, R'-Gal-R, is a β-glycoside:

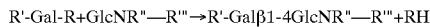

In the transglycosylation reaction,

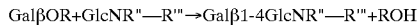

the reaction rate is higher than in the equilibrium reaction since the glycoside or disaccharide is more reactive than the non-activated sugar D-galactose used as donor in the equilibrium reaction. An enzyme of less purity, even a non-purified enzyme, can be used in the reaction since the enzymes are substrate/linkage specific and contaminating enzymes (e.g., α-galactosidase) will not react with GalβOR to give a β-linked product. Thus, intact cells (e.g. yeast) can be used as well as partially purified enzyme or enzyme of higher purity.

Hydrolysis of GalβOR will also occur to a certain extent depending on the reaction conditions. Lower or higher temperatures (e.g., room temperature or higher, e.g. 25°–65° C.) can be selected, organic (co)solvents (acetone, acetonitrile, tetrahydrofurane) can be used, the pH typically is selected from the range 4 to 8, the substrate concentrations are typically 30 mM to several M concentration (e.g. 7 M) depending on the solubility of the substrates, stability of enzyme in the reaction mixture, and the particular goal of the reaction and the type of substrates.

The reaction will go through a maximum of product formation and has to be followed (e.g., preferably by HPLC) and terminated after an appropriate time by e.g. heat treatment at e.g. 80°–100° C. for e.g. three minutes. Generally, donor consumption is tracked and the reaction terminated after a suitable time, which depends on the conditions, and often at ≧40% consumption of the donor. The reaction can be carried out for a few minutes to several hours depending on the growth of yeast cells (if fermentation conditions are used), the amount of enzyme, temperature, pH, concentration of substrates, and other factors.

The reaction can be monitored by means of TLC, HPLC or by spectrophotometric measurement of liberated aglycon (e.g. nitrophenol, 400 nm). Charring of TLC plates with sulfuric acid may be used for detection of sugars. When a desired yield of the product has been obtained, the reaction is terminated by denaturation of the enzyme by for example heat treatment. Heating to 85° C. or above for 3–5 min (eventually followed by addition of ethanol to a concentration of about 80%) is usually sufficient. If immobilized enzyme is used, the reaction may be terminated by centrifugation or filtration.

In each type of reaction depicted above, a D-glucopyranosamino derivative is used as acceptor (GlcNR"—R'") where R" and R'" are defined below.

In the case of N-acetyl-glucosamine (R"=—HAc group in the 2 position, i.e. in the N-position of 2-glucosamine; the 2-position in glucosamine contain a —NHAc), R'" represents an aglycon other than the anomeric hydroxyl group (i.e. R'" is not OH). If R" is not a —HAc group then R'" can be OH but can also represent a modification of the anomeric hydroxyl group as in the case where R" is —HAc.

The method according to the invention can be used to produce Galβ1-4GlcNR"—R'" in high purity (no other linkages observed by 400 MHZ NMR), a product which after isolation can be used for biological/therapeutical purposes or for further synthesis according to the invention. The method can also be used to produce Galβ1-4Galβ1-4GlcNR"—R'". Thus, with the same enzyme and in a further reaction one will obtain Galβ1-4Galβ1-4GlcNR"—R'" as shown by the following equation:

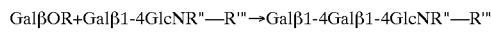

GlcNR"—R'", (the derivative of glucosamine which is used as acceptor), is of the general structure shown in the example below:

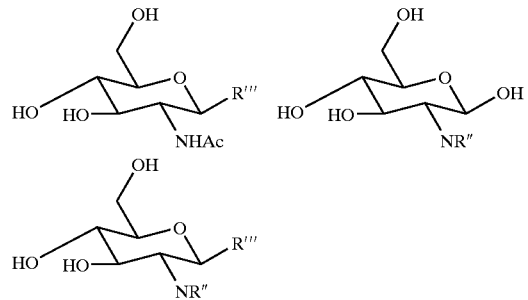

where NR" may be selected from compounds containing an inorganic group (e.g. $N_3$, $NHSO_3H$) and/or an organic group bound to the 2 position of glucosamine, such as (a) N-phthalimido; (b) an organic carbonyl group NH—C(O)—R where R is a hydrogen or a compound containing an organic group, e.g. aliphatics such as alkyl (e.g. methyl, ethyl, propyl), alkoxy (e.g. methoxy, ethoxy), allyloxy, amino acid or polypeptidyl is residue, and/or aromatics such as phenyl, benzyl or phenyloxy, preferred examples include N-chloromethoxyacetyl, N-phenoxyacetyl, NHBoc (Boc=t-butyloxycarbonyl), NHAc and NHC(O) $(CH_2)_n CH_3$ (n is an integer equal to or greater than 1); (c) NHR where R is a compound containing an aliphatic and/or J aromatic group as described above, for example lower alkyl, preferred examples include $NH(CH_2)_n CH_3$ (n is an integer equal to or greater than 1); or (d) NRR' where R and R' are independently selected from compounds containing an aliphatic and/or aromatic group as described above; preferably NR" is azido, 2-N-acetyl-, or 2-N-phthalimido;

and where R'" is selected from a glycosidically bound inorganic compound, e.g. fluoro or is selected from an O-, C-, N- or S-glycosidically bound compound containing an aliphatic and/or aromatic group, for example lower alkoxy (e.g. methyloxy (—OMe), ethyloxy (—OEt)), lower thioalkyl (e.g. β-linked thioethyl (—SEt)), thioaromatic (e.g. thiophenyl-), —OEtBr, nitrophenoxy, amino acid, peptide, or derivative thereof, or another organic group of interest for the use of the product, or R'" can be —OH if NR" is not NHAc but R'" is not —OH if NR" is NHAc.

The Galβ1-4GlcN (lactosamine) containing product obtained with GalβOR as donor in the method according to the present invention is of the general structure shown in the example below:

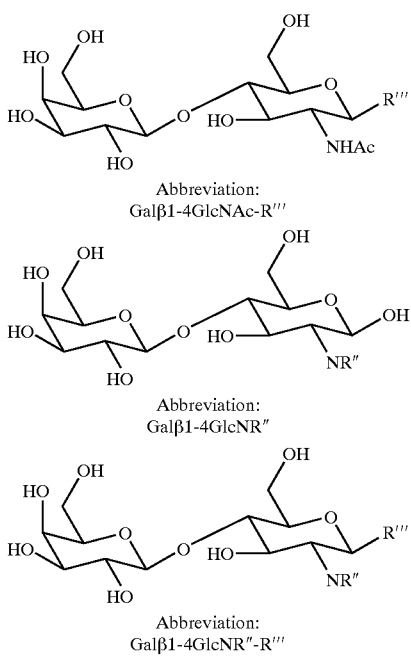

Abbreviation:
Galβ1-4GlcNAc-R'''

Abbreviation:
Galβ1-4GlcNR''

Abbreviation:
Galβ1-4GlcNR''-R'''

Such conjugates where lactosamine, or higher oligosaccharides containing the lactosamine structure, is N- or O-glycosidically bound to amino acids or peptide sequences, via the glucosamine residue in lactosamine and derivatives thereof as described above, are of interest to produce synthetically for fundamental studies and for synthesis of biologically/medically active fragments of glycoproteins, for instance to be used as vaccine or therapeutics. It is also important to be able to synthesize oligosaccharide analogues/derivatives of the structures above and according to the present invention to modify or improve the biological activity of the conjugate.

The synthetic procedure according to the invention can be carried out under highly diverse conditions in regards to, for example, pH, type of buffer, temperature and concentration of the reactants. Various cosolvents (N,N-dimethyl formamide, acetonitrile, dimethyl sulfoxide, dioxane, pyridine, methanol, ethanol, ethylene glycol, etc.) may be used and in varying concentrations together with water. In general, hydrophobic acceptor substances are more easily dissolved by the use of organic cosolvents or increased temperature. Moreover, the reactions may be carried out in two-phase systems, e.g. water-organic solvent or in two-phase systems of water-water polymer. The use of acceptors modified with organic groups facilitates recovery of the product in the organic phase.

The reaction conditions are not critical but are selected primarily on the basis of the properties of the reactants employed in the synthesis concerned, and also on the basis of practicality. For example, it may be mentioned that it is usually convenient to use a reaction temperature in the range of 25–75° C. and, in the case of water-rich medium, the pH is usually in the range 4–8.

The reaction temperature may also be varied to influence product yield and the activity and stability of the enzyme and does not restrict the scope of the invention. The temperatures most frequently used lie in the range 4–75° C., but lower temperatures and temperatures below 0° C. can be used which can be facilitated if organic cosolvent is used. An advantage with high temperatures is, for example, that high substrate concentrations may be used, which reduces the water activity and thus increases the yield of product. Another advantage is that the activity of the enzyme increases, which means shorter reaction times at increased temperatures. The upper temperature limit is determined by the thermostability of the enzyme and substrate in the specific reaction medium. In some reactions the thermostability of the enzyme is increased by the use of high sugar substrate concentration. High concentration of substrate e.g. lactose (>15% w/w) can be achieved by dissolving in hot buffered water followed by cooling to the desired reaction temperature.

The concentration of the acceptor is a parameter which can be used to influence the yield of the reactions according to the invention. High concentrations are usually preferable in both equilibrium and transglycosylation reactions to minimize hydrolytic side-reactions, which usually means that depending on the solubility of the acceptor, ca. 0.05–7 M concentration of acceptor is used. In general, high concentrations of substrates are obtained by heating the reaction mixture to near the boiling point for a few minutes, allowing the solution to cool to the reaction temperature (usually 4–75° C., depending on the temperature for optimum yield and thermostability of the enzyme/substrate) followed by addition of the enzyme. Cosolvents can be used to increase the solubility of substrates with hydrophobic groups.

The concentration of glycosyl donor in the reaction mixture is selected with regard to the lactosamine derivative to be synthesized and also with regard to the properties of the enzyme and therefore do not restrict the use of the invention. In some cases, addition of the donor in small portions may be advantageous in order to minimize the risk that the donor also acts as an acceptor (unless this is desired). Lactose is generally used as the donor since it is a cheap substrate. The weight ratio of donor to acceptor is preferably ≧1:1 though the acceptor can be in excess.

The enzyme may be used in situ or after partial or complete purification from its natural environment. The enzyme may be isolated before use by e.g. homogenization, precipitation and/or chromatography (e.g. based on ion-exchange, affinity, size). The enzyme may be present in e.g. soluble, immobilized, cross-linked, crystalline form or be enclosed within micelles. Generally, the glycosidase can be used in vivo or in vitro in a more or less purified form and in different cell types (as cloned into a suitable cell type). The enzyme may be produced with recombinant techniques. Then, if desired, one or more of the amino acids in the amino acid sequence of the enzyme may be changed in order to optimize the properties of the enzyme, e.g. thermostability, catalytic efficiency and/or stability in organic solvents. Variants of the glycosidase produced with recombinant technology which have at least 70% homology with the peptide chain of the natural variant are, together with the naturally occurring glycosidase, also useful according to the invention.

The synthetic reaction can be carried out with enzyme in vivo, that is under fermentation conditions with intact yeast cells and with lactose and acceptor in concentrations, for example, in the range 0.5 to 25% weight/volume. An excess of lactose is useful in some cases to improve the galactosylation of the acceptor and/or to prepare trisaccharides of the type mentioned above. This and other fermentation conditions with the necessary nutritional media/salts are easily determined by a person skilled in the art and does not limit the scope of the invention.

As glycosyl donor, lactose may be used or a β-glycoside of galactose such as an alkyl or aromatic glycoside (e.g. nitrophenyl β-galactoside).

Isolation of the product may be carried out in one or more steps involving one or more of the following procedures: extraction, chromatography (common solid supports that can be applied are e.g. Sephadex®, silica, reversed-phase silica, charcoal, charcoal-celite), precipitation.

Depending on if intact yeast cells (fermentation conditions) or if crude, partially isolated or isolated enzyme are used and also with regard to the solubility and stability of substrates, the reaction may be carried out at different conditions and preferably under conditions most suitable for the particular reaction. Such conditions are chosen by the person skilled in the art and do not limit the scope of the invention. Conventional pH (e.g. 4–8 obtained by e.g. acetate or phosphate buffer) and at low temperature, room temperature or at increased temperatures (e.g. in the range 0–50° C.) may be use if a crude, partially isolated, or isolated enzyme preparation is employed.

The reaction can be carried out in the presence of inert organic cosolvents in order to increase the solubility of the acceptor (e.g. hydrophobic acceptor) or to avoid hydrolysis reactions. If organic cosolvents (e.g. acetone, acetonitrile, tetrahydrofurane) are used together with buffered water as solvent for the reactions, lower temperatures than 0° C. (e.g. −30° C.) may be chosen in certain cases. The concentration of substrates are then usually in the range of 30 mM–7 M.

The enzyme may be used in soluble form or may be immobilized by e.g. adsorption, encapsulation, chelation, precipitation or covalent binding to a solid support, such as a polymeric substance, or a derivative thereof which is insoluble in protic or aprotic solvents (Methods in Enzymology, vol. 135, Academic Press). The form selected is not critical to the invention. If the enzyme is used in soluble form, it may if desired first have been chemically modified in a suitable manner in order to e.g. increase the thermostability or the stability in organic cosolvents. Enzyme immobilized to an insoluble polymer comprising, for example, agarose, cellulose, hydroxyethyl acrylate, glass, silica, polyacrylic amide, polyacrlyate-based plastics, etc., is readily separated from the product mixture, and the enzyme may thus be reused.

Examples of immobilization are adsorption or covalent binding of the enzyme to a suitable solid phase such as glass, celite, silica, polysaccharides (e.g. cellulose, agarose), or plastics (e.g. polystyrene), activated with a suitable reactive group for covalent binding of the enzyme as is known in the art (see e.g. Methods in Enzymology, volumes 44, 104 and 135).

If intact yeast cells are used, the reaction conditions are chosen by the person skilled in the art and do not limit the scope of the invention. Preferable conditions are normally pH 4–7, 20–35° C. in buffered water containing nutrients for the yeast cells as exemplified in the non-limiting examples below.

Microorganisms which produce enzymes with the same structure or of a similar structure (e.g., containing similar three dimensional tertiary structure and active site structure) as the one from *Bullera singularis* can also be used.

If high concentrations of lactose are used, a considerable amount of glucose will be formed when a crude, partially purified or isolated enzyme is used (under fermentation conditions with intact yeast cells the yeast will consume a large amount of the formed glucose). The formed glucose will compete with the acceptor (and with water) for the galactosyl-enzyme intermediate, thus inhibiting the synthesis of product. A second enzyme which specifically removes glucose may thus be used during the reaction according to the invention, such as an isomerase (e.g. glucose isomerase) or an oxidase. Also, the product may be removed by the use of another specific enzyme, transferase, sulfatase which specifically converts the product to another desired product, thereby minimizing secondary hydrolysis of product and/or avoiding the need for isolation of the lactosamine product prior to its use in further synthesis.

The products can be used for further enzymatic synthesis with glycosidases or glycosyltransferases. For example, α-sialyltransferase can be used to catalyze the formation of sialylated Gal-GlcNAc derivatives and α-fucosyl transferase can be used to form oligosaccharide derivatives of the type Gal-(Fuc)GlcNAc-R, which then can eventually be sulphated, sialylated and/or be used for further chemical synthesis, etc.

The products obtained with the method according to the invention may be used directly for biological applications or may be used for further synthesis to obtain various lactosamine group containing products employing enzymatic and/or chemical methods (see e.g. Example 7 below) of interest for e.g. various clinical, diagnostic, downstream processing or for food supplement purposes. For references to chemical modification of glucosamine and examples of possible chemical conversions of modified lactosamines see e.g. Binkley: Modern Carbohydrate Chemistry, Marcel Dekker, 1988 with references; Paulsen, Chem. Soc. Rev. 13, pages 15–45; Khan and Hindsgaul in Molecular Glycobiology, pages 206–229, Fukuda and Hindsgaul Editors, IRL Press, Oxford. For a reference to the use of thioethyl glycosides in the synthesis of various glycosides or for use as glycosyl donors in convergent block synthesis of tri-, tetra- and larger saccharides, see e.g. references cited in the Khan and Hindsgaul article.

The product obtained according to the invention may also be converted by enzymatic methods using e.g. lipases, sulfatases, glycosyltransferases and oxidases. In this way hydroxyl groups of the galactosyl or glucosaminyl moiety may be selectively modified with e.g. acyl groups, sulphate groups, saccharide groups and other organic groups respectively, thus further extending the utility of the method of the invention for preparation of different derivatives and higher saccharides containing the lactosamine group. Specific examples are the selection of a suitable lactosamine derivative prepared by the method according to the invention for reaction with e.g. a sialyltransferase or sulfatase to obtain e.g. an (α2-3) sialylated lactosamine derivative or a 3'-O-sulphated derivative containing the lactosamine group, respectively. For references to enzymatic modifications, see e.g. Khan and Hindsgaul above (glycosyltransferases) and Wang and Whitesides in Enzymes in Synthetic Organic Chemistry, Pergamon (1994), Elsevier Science LTd.; see also Enzyme Nomenclature, Academic Press (1984).

The aglycon of the lactosamine containing product obtained according to the invention may not only be used in glycosylation reactions (for formation of other glycosides or for synthesis of oligosaccharides containing the lactosamine sequence) but may also be used for covalent binding to another molecule such as a protein, bead or a solid support and the resulting product may then be used for various purposes. Thus, nitrophenyl glycosides are for example useful after reduction to aminophenyl glycoside for covalent binding to various proteins or solid supports, which then may be used in diagnostic reagents, in down stream processing for separation of various proteins and enzymes including glycosyltransferases with specificity of various proteins and enzymes including glycosyltransferases with specificity of acceptors containing the lactosamine sequence or for solid phase synthesis of oligosaccharides (see e.g.

Wong and Whitesides above for references to solid phase synthesis of oligosaccharides).

The following examples are illustrative of the invention:

EXAMPLE I

The synthesis of Galβ1-4GlcNPhtβSEt can be carried out as follows:

*Bullera singularis* is cultivated at 25° C. during stirring in a medium of the following composition: 5% lactose, 1% GlcNPhtβSEt, which has been sterile filtered with yeast extract (Difco, 0.75% w/w in sodium acetate, pH 5.0). The reaction is carried out at 27° C. until the lactose has been consumed to an appropriate extent. The product is isolated to homogeneity (no other sugar detected according to NMR) by the following procedure: after separation of yeast cells by centrifugation (or filtering), extraction of the water-phase with ethyl acetate to remove excess of acceptor, followed by butanol extraction of the water-phase and evaporation of the butanol-phase, followed by dissolution of the residue in water-ethanol, evaporation of ethanol, and precipitation of the product from water.

Isolation of the product is carried out for example by extraction of the water-phase with a suitable solvent, e.g. ethyl acetate, which removes unreacted acceptor and the water-phase can then be extracted with a more polar solvent such as n-butanol. Precipitation of product from the medium such as water can be used for further purification. Examples of other separation methods which can be used in combination with extraction is column chromatography, using typical materials such as silica, active carbon or Sephadex® as the solid phase, and precipitation or crystallization. Any suitable separation method known in the art can be used.

An important advantage with the enzymatic method according to the invention is that the acceptor is not destroyed (especially when mild reaction conditions and isolated enzyme are used), as might happen with unmodified acceptors or when chemical methods are used for synthesis. The non-reacted acceptor can therefore usually be recovered by e.g. the straightforward extraction procedure above.

EXAMPLE 1

Synthesis of Galβ1-4GlcNPhtβ-SEt (Compound I) (SEt=SCH$_2$CH$_3$ Group)

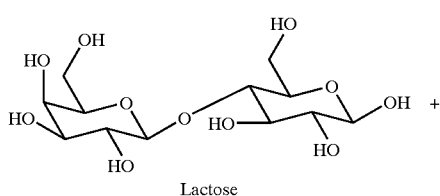
Lactose

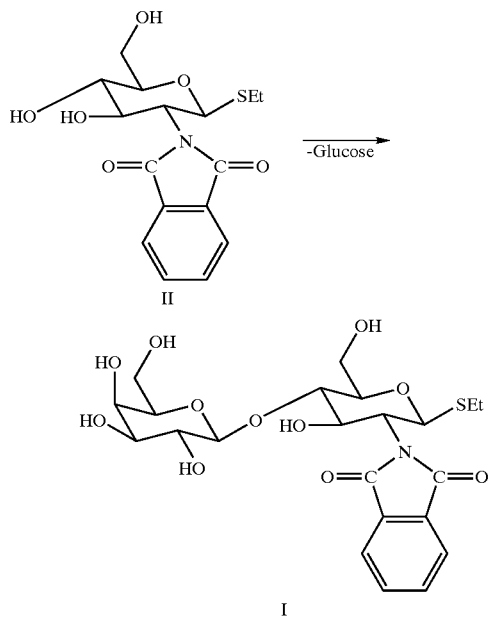

Typically, Compound I was prepared in a fermentation reaction or with a partially purified β-galactosidase preparation (obtained after disintegration of yeast cells under high pressure (600 bar)) and centrifugation of the solid material which was then used for synthesis). In a typical reaction, the initial concentration of lactose (glycosyl donor) and GlcNPhtβ-SEt (acceptor; compound II) were 5 and 1.2% (w/V), respectively in yeast medium (as described above). Yeast cells (*Bullera singularis*) were added (OD600 was ca 1 after addition of the yeast cells) and the fermentation was carried out at 27° C. with moderate shaking (150 rpm) at pH 5.5 for five days. Alternatively, the partially purified galactosidase preparation was used as catalyst for the reaction. Instead of lactose as the glycosyl donor, the β-linked nitrophenyl glycoside of galactose (e.g. Galβ-OPhNO$_2$-o or Galβ-OPhNO$_2$-p) can be used as glycosyl donor.

The reaction was followed by TLC and by measurement of liberated nitrophenol at 405 nm (for nitrophenyl substrates). For each of the above reactions, isolation of product was achieved by extraction of II with ethyl acetate, extraction of product with butanol, evaporation of solvent followed by chromatography (typically Sephadex® G10) and/or crystallization.

The product was identified by NMR (400 MHz, Jeol) and the linkage positions determined in the peracetylated form with standard procedures (characteristic shifts of linkage positions determined by $^1$H—$^1$H COSY NMR). Selected NMR-data ($^{13}$C; non-corrected) for product I:

Disaccharide part of product: 103.93 (C'-1), 80.32 (C-1), 70.21 (C-3), 79.61 (C-4), 55.65 (C-2); Phthalimido group: 123.33, 123.61, 130.76, 130.96, 135.02, 135.09, 167.39 and 167.63 (2 C=O groups); SEt group: 14.92 and 23.27.

EXAMPLE 2

Synthesis of Galβ1-4GlcNPhtβ-OMe (Compound III OMe=OCH₃)

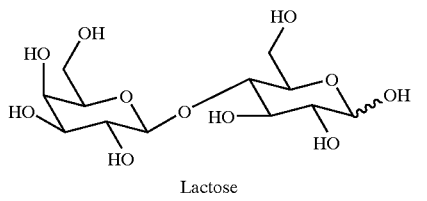

Lactose

+

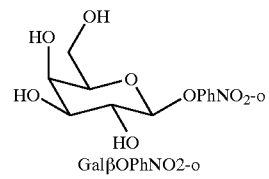

GalβOPhNO2-o

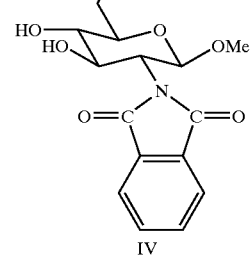

IV

→ -Glucose

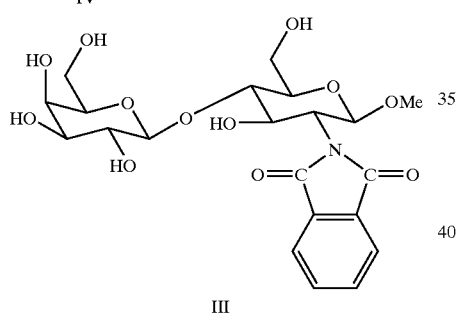

III

Typically, Compound III was prepared as in Example 1 in a fermentation reaction or with a crude β-galactosidase preparation (obtained after disintegration of yeast cells in sodium acetate, 50 mM, pH 5, under high pressure at 600 bars). Centrifugation gave a solid material which was used for synthesis. In a typical reaction, the initial concentrations of lactose (glycosyl donor) and GlcNPhtβ-SEt (acceptor; compound IV) were 7 and 2.5% (w/V), respectively, in 40 ml of 50 mM sodium acetate, pH 6.0. Crude β-galactosidase preparation were added (ca 3 g) and the reaction was carried out at 30° C. with gentle agitation at pH 6.0 for two days. Instead of lactose as the glycosyl donor, the β-linked nitrophenyl glycoside of galactose, Galβ-OPhNO₂-o, was used as glycosyl donor (0.15 M)

The reaction was followed by TLC and by measurement of liberated nitrophenol at 405 nm (for nitrophenyl substrates). For each of the above reactions, isolation of product was achieved by extraction of IV with ethyl acetate, followed by chromatography and freeze-drying. In this way, product I was obtained and non-reacted acceptor was recovered and could be reused.

The product was identified by NMR (400 MHz, Jeol) and the linkage positions determined with standard procedures (characteristic shift of linkage positions determined by ¹H—¹H COSY NMR). Selected NMR-data ($^{13}C$; non-corrected) for product III:

Disaccharide part of product: 103.94 (C'-1), 99.90 (C-1), 70.44 (C-3), 79.96 (C-4), 57.03 (C-2);

Phthalimido group: 123.71, 124.44, 131.68 (2C), 135.89 (2C), 170.36 (2C; C=O);

Methyl group: 57.44.

EXAMPLE 3

Synthesis of Galβ1-4GlcNPht (Compound V)

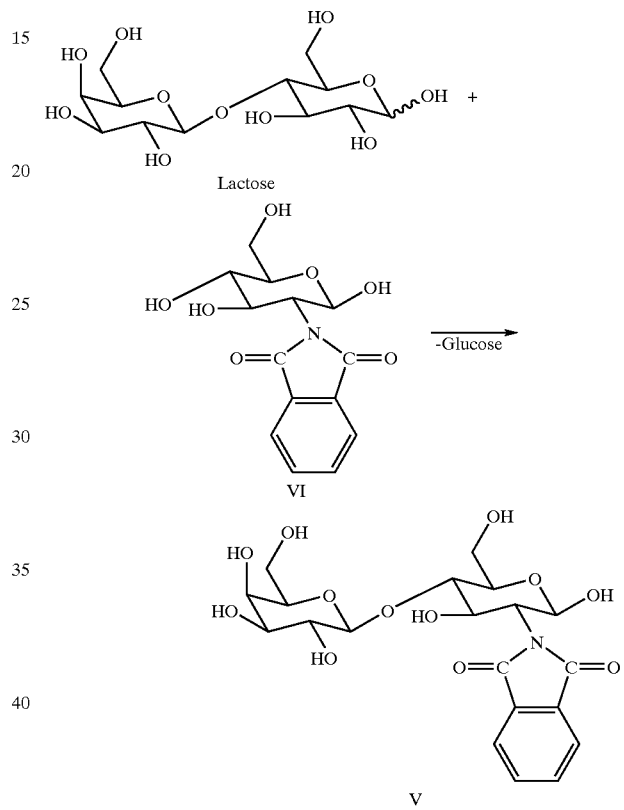

Typically, Compound V was prepared as in Example 1 in a fermentation reaction or with a crude β-galactosidase preparation (obtained after disintegration of the yeast cells suspended in sodium acetate, 50 mM, pH 5, under high pressure (600 bar)) and centrifugation gave a solid material which was used for synthesis). In a typical reaction, the initial concentrations of lactose (glycosyl donor) and GlcN-Pht (acceptor; compound VI) were 7 and 3% (w/V), respectively, in 75 ml of 50 mM sodium acetate, pH 6.0. Crude β-galactosidase preparation were added (ca 6 g) and the reaction was carried out at 30° C. with gentle agitation at pH 6.0 for two days. Instead of lactose as the glycosyl donor, the β-linked nitrophenyl glycoside of galactose, Galβ-OPhNO₂-o, was used as glycosyl donor.

The reaction was followed by TLC and by measurement of liberated nitrophenol at 405 nm (for nitrophenyl substrates). For each of the above reactions, isolation of product was achieved by chromatography (Sephadex and C18-silica).

The product was identified by NMR (400 MHz, Jeol) and the linkage positions determined with standard procedures (characteristic shift of linkage positions determined by $^1$H—$^1$H COSY NMR). Selected NMR-data ($^{13}$C; non-corrected) for product V:

Disaccharide part of product: 105.14 (C'-1), 93.84 (C-1), 71.09 (C-3), 81.46 (C-4), 59.22 (C-2); Phthalimido group: 124.04, 124.27, 133.05 (2C), 135.50 (2C), 169.76 (2C; C=O).

EXAMPLE 4

Synthesis of Galβ1-4GlcN$_3$β-OMe (Compound VII; N$_3$=Azido Group):

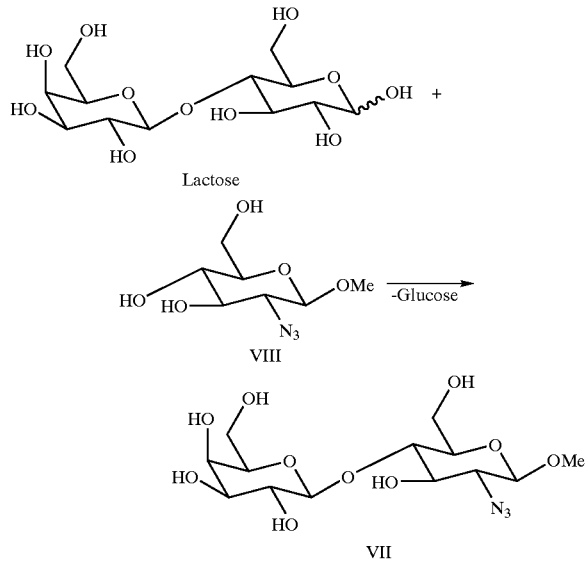

Typically, Compound VII was prepared as in Example 1 in a fermentation reaction or with a crude β-galactosidase preparation (obtained after disintegration of yeast cells in sodium acetate, 50 mM, pH 5, under high pressure (600 bar) and centrifugation gave a solid material which was then used for synthesis). In a typical reaction, the initial concentrations of lactose (glycosyl donor) and GlcN$_3$β-OMe (acceptor; compound VIII) were 7 and 3% (w/V), respectively, in 75 ml of 50 mM sodium acetate, pH 6.0. Crude β-galactosidase preparation were added (ca 6 g) and the reaction was carried out at 30° C. with gentle agitation at pH 6.0 for two days. Instead of lactose as the glycosyl donor, the β-linked nitrophenyl glycoside of galactose, Galβ-OPhNO$_2$-o, was used as glycosyl donor.

The reactions were followed by TLC and by measurement of liberated nitrophenol at 405 nm (for nitrophenyl substrates). For each of the above reactions, recovery of non-reacted substrates and isolation of product was achieved by chromatography (C18-silica Sephadex).

The product was identified by NMR (400 MHz, Jeol) and the linkage positions determined in the peracetylated form with standard procedures (characteristic shift of linkage positions determined by $^1$H—$^1$H COSY NMR). Selected NMR-data ($^{13}$C; non-corrected) for product VII:

Disaccharide part of product: 103.87 (C'-1), 102.90 (C-1), 73.44 (C-3), 79.12 (C-4), 66.03 (C-2); Methyl group: 58.11.

EXAMPLE 5

Synthesis of Galβ1-4GlcNAcβ-SEt (Compound IX)

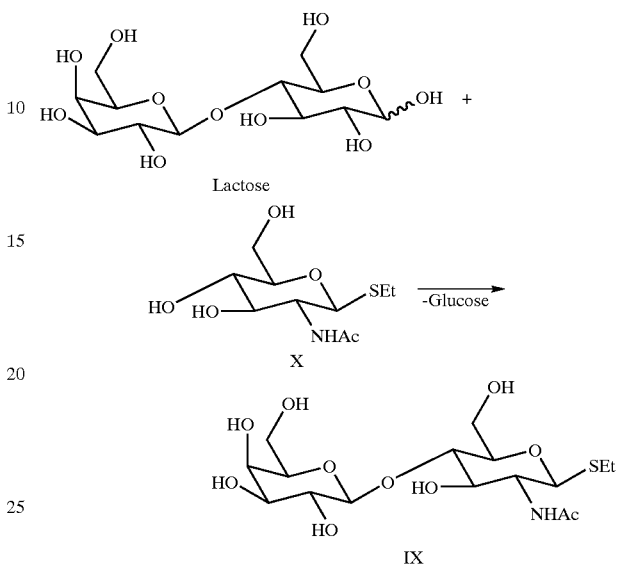

Typically, Compound IX was prepared as in Example 1 in a fermentation reaction or with a crude β-galactosidase preparation (obtained after disintegration of yeast cells in sodium acetate, 50 mM, pH 5, under high pressure (600 bar) and centrifugation gave a solid material which was then used for synthesis). In a typical reaction, the initial concentrations of lactose (glycosyl donor) and GlcNAcβ-SEt (acceptor; compound X) were 7 and 5% (w/V), respectively, in 75 ml of 50 mM sodium acetate, pH 6.0. Crude β-galactosidase preparation were added (ca 6 g) and the reaction was carried out at 30° C. with gentle agitation at pH 6.0 for two days. Instead of lactose as the glycosyl donor, the β-linked nitrophenyl glycoside of galactose, Galβ-OPhNO$_2$-o, was used as glycosyl donor.

The reactions were followed by TLC and by measurement of liberated nitrophenol at 405 nm (for nitrophenyl substrates). For each of the above reactions, recovery of non-reacted substrates and isolation of product achieved by chromatography (Sephadex) and crystallization. In this way, product IX was obtained and non-reacted substrates were recovered and could be reused.

The product was identified by NMR (400 MHz, Jeol) and the linkage positions determined with standard procedures (characteristic shift of linkage positions determined by $^1$H—$^1$H COSY NMR). Selected NMR-data ($^{13}$C; non-corrected) for product IX:

Disaccharide part of product: 103.76 (C'-1), 84.85 (C-1), 76.27 (C-3), 74.66 (C-4), 61.93, 61.14 (C-6,6'), 55.24 (C-2), 175.30 (C=O from NHAC group); 25.39, 23.13, 15.21 (SEt group and methyl group in NHAc).

EXAMPLE 6

Synthesis of Galβ1-4GlcNAcβ-OPhNO₂-p (Compound XI)

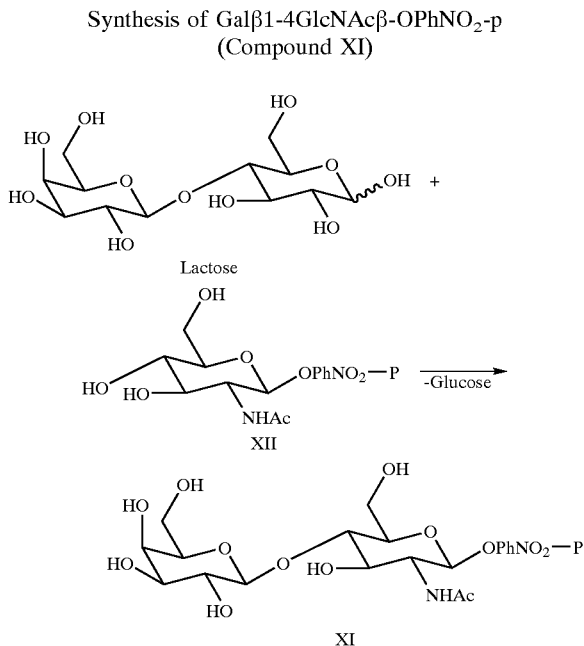

Typically, this compound was prepared from lactose (7% w/w) and with p-nitrophenyl β-D-N-acetyl-glucosaminide (0.6% w/w) as acceptor employing a crude β-galactosidase obtained as described above at 30° C. for two days. The compound was isolated by extraction with ethyl acetate followed by column chromatography (Sephadex G10) of the water phase. The product was characterized by NMR as described above.

In all the above reactions, the disaccharide glycoside Galβ1-4Galβ-OPhNO₂-o was obtained as an additional product when Galβ-OPhNO₂-o was used as donor.

The acceptor substance in Examples 1–3 were prepared by standard chemical techniques known to the person skilled in the art from 2-amino-2-deoxy-D-glucosamine (GlcNH₂) via the peracetylated phthalimido derivative (peracetylated GlcNPht). The azido acceptor substrate in Example 4 was prepared from glucose via the glucal followed by azidonitration according to standard chemical techniques known to the person skilled in the art. The acceptor substrates in Examples 5 and 6 were obtained via peracetylated GlcNAc by standard chemical techniques known to the person skilled in the art.

The compounds prepared above are of interest for use either for direct use in biological application or for synthesis of other lactosamine derivatives, higher oligosaccharides (R1=saccharide; R2 may be H2, acetyl or other group: other R are OH), and/or for conjugation to other type of molecules including proteins, antibodies, peptides, amino acids and enzymes (R1=protein, antibody, peptide, amino acid, modified amino acid, or enzyme glycosidically bound to the lactosamine sequence).

EXAMPLE 7

Synthesis of Product

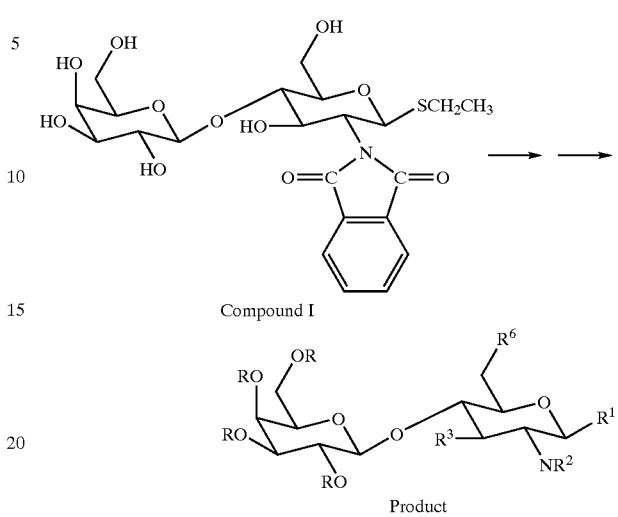

Peracylation or other modification of compound I, III or V with standard chemical techniques gives after isolation a protected compound with a free 3-OH group in the glucosamine part. Such a modified compound can be used for production of Lewis-x compounds (Lewis-x =Galβ1-4 (Fucα1-3)GlcNAc; $R^3$ in the figure above is an α-linked fucopyranosyl group; $R^2$ is an acetyl group and RO groups are HO-groups) and derivatives as well as other compounds modified in the 2-N group, 3-OH group ($R^3$=other sugar than L-fucose, e.g. instead of α-fucopyranosyl the 3-OH position can be modified with another sugar, mannose, galactose, etc. bound in α- or β-configuration or with another group), and/or, in the anomeric position of the glucosamino-residue the thioethyl disaccharides are routinely used for synthesis of other disaccharide glycosides such as amino acid glycosides ($R^1$=amino acid) or as a glycosyl donor with acceptor saccharides for convergent block synthesis of tri- or higher oligosaccharides.

Thus, for chemical preparation of Lewis-x and derivatives thereof Compound I, III or V can first be partially modified in the hydroxyl groups via e.g. peracetylation (pyridine+ acetic anhydride). This gives after separation from other products the peracetylated compound I, III or V with a free 3-hydroxyl group and a —SEt, —OMe or OAc group, respectively, in $R^1$. The resulting compound can then be reacted with a fucopyranosyl compound (e.g. peracetlyated L-fucopyranose) to give a Lewis-x derivative. After removal of the R groups and other protection groups and acetylation of the NH₂-group Galβ1-4(Furα1-3)GlcNAc (Lewis-x) is obtained.

More specifically, the thioethyl group of Compound I (Galβ1-4GlcNPhtβ-SEt), or preferably the peracetylated Compound I (IB), can be converted to peracetylated Galβ1-4GlcNPhtβOR¹ or Galβ1-4GlcNPhtβSR¹ where $R^1$ is an organic compound including a mono-, di- or higher oligosaccharide. The N-phthalimido group may be removed by standard techniques known in the art (e.g. hydrazine) and the NH2 group formed may be used for conversion to, for example, Galβ1-4GlcNC(O)R where R is methyl, ethyl or other organic group (see definition of NR" above), or Galβ1-4GlcNR where R is an inorganic group (e.g. sulfate) or a compound containing an organic group (aliphatic and/or aromatic).

Compound I can be e.g. peracetylated (pyridine+acetic anhydride) to form a compound (IB) of the type below:

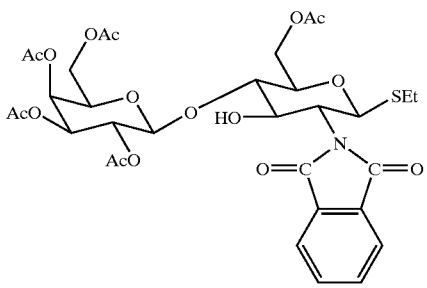

Compound IB can be reacted with e.g. peracylated L-fucopyranose to form Compound IC:

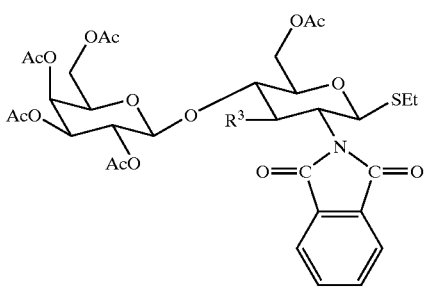

Another modified form of IB, L-fuc or another sugar than fucose might be selected to give other compounds or higher yields.

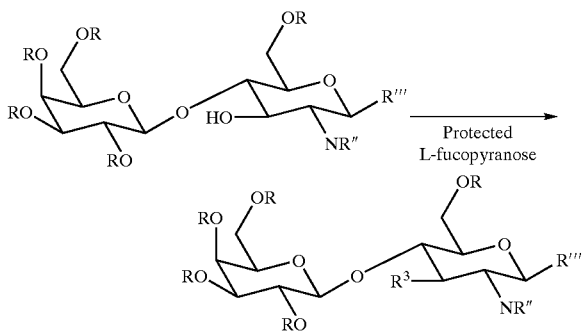

Other types of protection groups may be selected by the person skilled in the art to achieve higher yields.

The acetyl groups and phthalimido group of Compound IC can be removed by standard techniques and the NH2 group acetylated to form Compound ID (Galβ1-4(Fucα1-3)GlcNAcβSEt; thioethyl glycoside of Lewis-x); SEt can also be removed to form Compound IE (Galβ1-4 (Fucα1-3) GlcNAc; Lewis-x).

The phthalimido group of Compound IC can be removed and the NH2 group coupled to R-X and/or the -SEt group is used for coupling to sugar or hydroxyl group containing compound $R^1OH$ to form Compound IF (Galβ1-4(Fucα1-3) GlcNR"-$R^1$; a derivative of Lewis-x) where R is an inorganic or organic group and $R^1$ is a sugar, —OH, or organic group including amino acids or peptides.

EXAMPLE 8

Chemoenzymatic Modification to Obtain Lactosamine Containing Product

Several glycosyltransferases (belonging to EC group 2.4) such as Galβ1-3/4GlcNAcα2-3sialyltransferase and Galβ1-3/4GlcNAcα3/4fucosyltransferase can transfer sialyl groups and fucosyl groups, respectively, to different types of lactosamine derivatives modified in the 2-N-position. Sialyl, abbreviated as NeuAc, is used herein as an abbreviation for structures of sialic acid and analogs of sialic acid which are transferred by sialyltransferase. Fucosyl, abbreviated as Fuc, is used herein as an abbreviation for structures of L-fucopyranose and analogs of L-fucopyranose which are transferred by fucosyltransferase.

Thus, a suitable lactosamine derivative prepared with *Bullera singularis* or glycosidase according to the invention may be selected (or as obtained after chemical or enzymatic conversion of a hydroxyl group, R" and/or R'" group of the enzymatically produced lactosamine derivative, e.g. by the use of lipase for partial acylation of e.g. the glucosamine part) by the person skilled in the art to use as an acceptor with α2-3sialyltransferase as catalyst and a suitable CMP-NeuAc as glycosyl donor to obtain the corresponding u2-3sialylated lactosamine derivative NeuAcα2-3Galβ1-4GlcNR"—R'".

Similarly, a suitable lactosamine derivative prepared with *Bullera singularis* or glycosidase according to the invention may be selected (or as obtained after chemical or enzymatic conversion of a hydroxyl group, R" and/or R'" group of the enzymatically produced lactosamine derivative, e.g. by the use of lipase for partial acylation of e.g. the glucosamine part) by the person skilled in the art to use as an acceptor with α1-3fucosyltransferase as catalyst and a suitable GDP-Fuc as glycosyl donor to obtain the corresponding α2-3sialyated lactosamine derivative Galβ1-4 (Fucα1-3) GlcNR"—R'".

Also, a combination of the two glycosyltransferase reactions with the lactosamine derivative as the first acceptor may be selected by the person skilled in the art and used to obtain a derivative of NeuAcα2-3Galβ1-4(Fucα1-3)GlcNR"—R'".

The above derivatives can then be converted to other derivatives (e.g. by chemical modification of R" and/or R'" groups as described above, or by further enzymatic reactions) The above derivatives may be used in the various types of applications described above as appropriate. Examples are in clinical, diagnostic, downstream processing applications.

Further variations and modifications of the foregoing will be apparent to those skilled in the art and such variations and modifications are attended to be encompassed by the claims that are appended hereto.

Swedish Priority Application 94 000346 filed on Jan. 6, 1994 is relied on and incorporated by reference.

What is claimed:

1. A method of producing a lactosamine containing compound with β1-4 linkage, said method comprising:
   (1) reacting
      (a) at least one donor substance selected from the group consisting of galactose and GalβOR, where R is an organic group, and
      (b) at least one acceptor substance which is a glucopyranosamino compound having the formula GlcNR"—R'",
         wherein NR" is an azido, 2-N-acetyl-, 2-N-phthalimido, or another compound containing an inorganic and/or organic group bound to the 2-N-group of glucosamine,
         wherein R'" is an O-, C-, — or S-glycosidically bound lower alkoxy selected from methyloxy and ethyloxy, a β-linked thioethyl, or a thiophenyl, (c) in the presence of *Bullera singularis* or an E.C. group 3.2 glycosidase producing the desired lactosamine containing compound with β1-4 linkage; and (2) optionally isolating said lactosamine containing compound with β1-4 linkage.

2. A method of producing a lactosamine containing compound with β1-4 linkage, said method comprising:

(1) reacting
   (a) at least one donor substance selected from the group consisting of galactose and GalβOR, where R is an organic group, and
   (b) at least one acceptor substance which is a glucopyranosamino compound having the formula GlcNR"—R''',
      wherein NR" is N-phthalimido, NH—C(O)—R, NHR or NRR' where R and R' are a group containing an organic and/or inorganic group,
      wherein R''' is a glysocidically bound fluoro or is an O-, C-, — or S-glycosidically bound aliphatic or aromatic compound,
      with the proviso that if NR" is NHAc then R''' is not OH and if NR" is not NHAc then R''' may be OH,
   (c) in the presence of *Bullera singularis* or an E.C. group 3.2 glycosidase producing the desired lactosamine containing compound with β1-4 linkage; and (2) optionally isolating said lactosamine containing compound with β1-4 linkage.

3. The method according to claim 1, wherein R and R' are a group containing an aliphatic and/or aromatic group.

4. The method according to claim 3, wherein said aliphatic group is a alkyl, alkoxy, or allyloxy and wherein said aromatic group is phenyl, benzyl or phenyloxy.

5. The method according to claim 4, wherein said alkyl is methyl, ethyl or propyl and said alkoxy is methoxy or ethoxy.

6. A method of producing a lactosamine containing compound with β1-4 linkage selected from the group consisting of Galβ1-4GlcNPhtβ-Set, Galβ1-4GlcNPhtβ-Ome, Galβ1-4GlcNPht, Galβ1-4GlcN$_3$β-Ome, and Galβ1-4GlcNAcβ-OphNO$_2$-p, the method comprising:

(1) reacting
   (a) at least one donor substance selected from the group consisting of galactose and GalβOR, where R is an organic group, and
   (b) at least one acceptor substance which is a glucopyranosamino compound having the formula GlcNR"—R''',
      wherein NR" is an azido, 2-N-acetyl-, 2-N-phthalimido, or another compound containing an inorganic and/or organic group bound to the 2-N-group of glucosamine,
      wherein R''' is a glycosidically bound fluoro or is an O-, C-, —or S-glycosidically bound aliphatic or aromatic compound,
      with the proviso that if NR" is NHAc then R''' is not OH and if NR" is not NHAc then R''' may be OH,
   (c) in the presence of *Bullera singularis* or an E.C. group 3.2 glycosidase producing the desired lactosamine containing compound with β1-4 linkage; and (2) optionally isolating said lactosamine containing compound with β1-4 linkage.

7. A method of producing a lactosamine containing compound with β1-4 linkage, said method comprising:

(1) reacting
   (a) at least one donor substance selected from the group consisting of galactose and GalβOR, where R is an organic group, and
   (b) at least one acceptor substance which is a glucopyranosamino compound having the formula GlcNR"—R''',
      wherein NR" is an azido, 2-N-acetyl-, 2-N-phthalimido, or another compound containing an inorganic and/or organic group bound to the 2-N-group of glucosamine,
      wherein R''' is a glycosidically bound fluoro or is an O-, C-, — or S-glycosidically bound aliphatic or aromatic compound,
      with the proviso that if NR" is NHAc then R''' is not OH and if NR" is not NHAc then R''' may be OH,
   (c) in the presence of *Bullera singularis* or an E.C. group 3.2 glycosidase producing the desired lactosamine containing compound with β1-4 linkage; and (2) optionally isolating said lactosamine containing compound with β1-4 linkage; and (3) adding a second enzyme, selected from an isomerase and an oxidase, which specifically removes glucose.

8. The method according to claim 7, wherein said isomerase is glucose isomerase.

9. A method of producing a lactosamine containing compound with β1-4 linkage, said method comprising:

(1) reacting
   (a) at least one donor substance comprising lactose, and
   (b) at least one acceptor substance which is a glucopyranosamino compound having the formula GlcNR"—R''',
      wherein NR" is an azido, 2-N-acetyl-, 2-N-phthalimido, or another compound containing an inorganic and/or organic group bound to the 2-N-group of glucosamine,
      wherein R''' is a glycosidically bound fluoro or is an O-, C-, — or S-glycosidically bound aliphatic or aromatic compound,
      with the proviso that if NR" is NHAc then R''' is not OH and if NR" is not NHAc then R''' may be OH,
   (c) in the presence of *Bullera singularis* or an E.C. group 3.2 glycosidase producing the desired lactosamine containing compound with β14 linkage; and (2) optionally isolating said lactosamine containing compound with β1-4 linkage.

10. A method for the production of Lewis-x compounds, said method comprising:

(1) reacting
   (a) at least one donor substance comprising lactose, and
   (b) at least one acceptor substance which is a glucopyranosamino compound having the formula GlcNR"—R''',
      wherein NR" is an azido, 2-N-acetyl-, 2-N-phthalimido, or another compound containing an inorganic and/or organic group bound to the 2-N-group of glucosamine,
      wherein R''' is a glycosidically bound fluoro or is an O-, C-, — or S-glycosidically bound aliphatic or aromatic compound,
      with the proviso that if NR" is NHAc then R''' is not OH and if NR" is not NHAc then R''' may be OH,
   (c) in the presence of *Bullera singularis* or an E.C. group 3.2 glycosidase producing the desired lactosamine containing compound with β1-4 linkage; and (2) optionally isolating said lactosamine containing compound with β1-4 linkage to form a peracetlyated compound;
reacting said peracetlyated compound with a fucopyranosyl compound; and
subsequently removing the R groups and acetylating the NH₂ group.

11. A method of producing a lactosamine containing compound with β1-4 linkage, said method comprising:
(1) reacting
(a) at least one donor substance comprising lactose, and
(b) at least one acceptor substance which is a glucopyranosamino compound having the formula GlcNR"—R'",
wherein NR" is an azido, 2-N-acetyl-, 2-N-phthalimido, or another compound containing an inorganic and/or organic group bound to the 2-N-group of glucosamine,
wherein R'" is a glycosidically bound fluoro or is an O-, C-, — or S-glycosidically bound aliphatic or aromatic compound,
with the proviso that if NR" is NHAc then R'" is not OH and if NR" is not NHAc then R'" may be OH,
(c) in the presence of an E.C. group 3.2 glycosidase obtained from a yeast, to form said lactosamine containing compound with β1-4 linkage; and
(2) optionally isolating said lactosamine containing compound with β1-4 linkage.

12. A method of producing a lactosamine containing compound with β1-4 linkage, said method comprising:
(1) reacting
(a) at least one donor substance comprising lactose, and
(b) at least one acceptor substance which is a glucopyranosamino compound having the formula GlcNR"—R'",
wherein NR" is an azido, 2-N-acetyl-, 2-N-phthalimido, or another compound containing an inorganic and/or organic group bound to the 2-N-group of glucosamine,
wherein R'" is a glysocidicaly bound fluoro or is an O-, C-, — or S-glycosidically bound aliphatic or aromatic compound,
with the proviso that if NR" is NHAc then R'" is not OH and if NR" is not NHAc then R'" may be OH,
(c) in the presence of a recombinant β-galactosidase with the amino acid sequence of an E.C. group 3.2 glycosidase obtained from a yeast, to form said lactosamine containing compound with β1-4 linkage.

13. A method of producing a lactosamine containing compound with β1-4 linkage, said method comprising:
(1) reacting
(a) at least one donor substance selected from the group consisting of galactose and GalβOR, where R is an organic group, and
(b) at least one acceptor substance which is a glucopyranosamino compound having the formula GLcNR"—R'",
wherein NR" is an azido, 2-N-acetyl-, 2-N-phthalimido, or another compound containing an inorganic and/or organic group bound to the 2-N-group of glucosamine,
wherein R'" is an O-, C-, — or S-glycosidically bound lower alkoxy selected from methyloxy and ethyloxy, a β-linked thioethyl, or a thiophenyl,
(c) in the presence of a crude, partially isolated or isolated form of E.C. group 3.2 glycosidase producing the desired lactosamine containing compound with β1-4 linkage; and
(2) optionally isolating said lactosamine containing compound with β1-4 linkage.

14. A method of producing a lactosamine containing compound with β1-4 linkage, said method comprising:
(1) reacting
(a) at least one donor substance selected from the group consisting of galactose and GalβOR, where R is an organic group, and
(b) at least one acceptor substance which is a glucopyranosamino compound having the formula GLcNR"—R'",
wherein NR" is N-phthalimido, NH-C(O)—R, NHR or NRR' where R and R' are a group containing an organic and/or inorganic group,
wherein R'" is a glycosidically bound fluoro or is an O-, C-, — or S-glycosidically bound aliphatic or aromatic compound,
with the proviso that if NR" is NHAc then R'" is not OH and if NR" is not NHAc then R'" may be OH,
(c) in the presence of a crude, partially isolated or isolated form of E.C. group 3.2 glycosidase producing the desired lactosamine containing compound with β1-4 linkage; and
(2) optionally isolating said lactosamine containing compound with β1-4 linkage.

15. A method of producing a lactosamine containing compound with β1-4 linkage, said method comprising:
(1) reacting
(a) at least one donor substance lactose, and
(b) at least one acceptor substance which is a glucopyranosamino compound having the formula GLcNR"—R'",
wherein NR" is an azido, 2-N-acetyl-, 2-N-phthalimido, or another compound containing an inorganic and/or organic group bound to the 2-N-group of glucosamine,
wherein R'" is a glycosidically bound fluoro or is an O-, C-, — or S-glycosidically bound aliphatic or aromatic compound,
with the proviso that if NR" is NHAc then R'" is not OH and if NR" is not NHAc then R'" may be OH,
(c) in the presence of an E.C. group 3.2 glycosidase obtained from a yeast, in crude, partially isolated or isolated form, to form said lactosamine containing compound with β1-4 linkage.

16. A method of producing a lactosamine containing compound with β1-4 linkage, said method comprising:
(1) reacting
(a) at least one donor substance lactose, and
(b) at least one acceptor substance which is a glucopyranosamino compound having the formula GLcNR"—R'",
wherein NR" is an azido, 2-N-acetyl-, 2-N-phthalimido, or another compound containing an inorganic and/or organic group bound to the 2-N-group of glucosamine,
wherein R'" is a glycosidically bound fluoro or is an O-, C-, — or S-glycosidically bound aliphatic or aromatic compound,
with the proviso that if NR" is NHAc then R'" is not OH and if NR" is not NHAc then R'" may be OH,
(c) in the presence of a recombinant β-galactosidase with the amino acid sequence of an E.C. group 3.2 glycosidase obtained from a yeast, in crude, partially isolated or isolated form, to form said lactosamine containing compound with β1-4 linkage.

* * * * *